United States Patent [19]

Nitoh et al.

[11] Patent Number: 4,943,661

[45] Date of Patent: Jul. 24, 1990

[54] PROCESS FOR PREPARING THIOUREA DIOXIDE DERIVATIVES

[75] Inventors: Hirohisa Nitoh; Osami Ohura; Morio Suzuki, all of Shizuoka, Japan

[73] Assignee: Tokai Denka Kogyo Kabushiki Kaisha, Tokyo, Japan

[21] Appl. No.: 323,495

[22] Filed: Mar. 14, 1989

[30] Foreign Application Priority Data

Sep. 30, 1988 [JP] Japan ............................ 63-243896

[51] Int. Cl.$^5$ ................. C07C 335/08; C07C 335/12; C07C 335/16
[52] U.S. Cl. ........................................ 564/26; 564/30

[58] Field of Search ................. 564/26, 30, 336, 395, 564/469

[56] References Cited

FOREIGN PATENT DOCUMENTS 2529200 12/1983 France .

*Primary Examiner*—Richard L. Raymond
*Assistant Examiner*—Peter G. O'Sullivan
*Attorney, Agent, or Firm*—Scully, Scott, Murphy & Presser

[57] ABSTRACT

An amine-substituted thiourea dioxide is obtained by reacting thiourea dioxide and an aliphatic or aromatic primary amine in a neutral or acidic pH range.

5 Claims, No Drawings

PROCESS FOR PREPARING THIOUREA DIOXIDE DERIVATIVES

BACKGROUND OF THE INVENTION

The present invention relates to a process for preparing an amine-substituted thiourea dioxide by the reaction of thiourea dioxide and a primary amine.

Since thiourea dioxide exhibits a strong reducing ability in a basic aqueous solution it is in wide use as a reducing agent in the dyeing industry and camera industry.

Further, in the field of polymers and that of organic chemistry, it has been studied to use thiourea dioxide as a stabilizer for various compounds (e.g. U.S. Pat. Nos. 2,472,868 and 3,070,569), as an amino resin curing agent (e.g. German Patent No. 1,215,363 and French Patent No. 1,445,045), or as a vinyl monomer polymerization initiator wherein thiourea dioxide is used together with iron-hydrogen peroxide [e.g. Am. Dyest. Rep. 75, 26–34 (1986)]. Thiourea dioxide has come to be applied to these uses gradually.

In the field of high polymers and that of organic chemistry, however, the application range of thiourea dioxide is limited because thiourea dioxide is insoluble in most organic solvents other than water. In these fields there are only extremely limited examples of industrial use of thiourea dioxide.

On the other hand, as to the method of preparing derivatives of thiourea dioxide, there has been proposed a method wherein thiourea derivatives such as N,N'-diphenylthiourea, N,N'-dibenzylthiourea and N,N'-dicyclohexylthiourea are oxidized with hydrogen peroxide to prepare the corresponding thiourea dioxide derivatives, as described in J. Chem. Soc. Perkin II, 4, 1500 (1972) and Synth. Commun. 4, 389 (1974). But this method is of less industrial utility because it is difficult to obtain the starting thiourea derivatives industrially.

It is the object of the present invention to overcome the above-mentioned drawback of the prior art and provide a process for effectively preparing an amine-substituted thiourea dioxide of great utility value.

It is described, for example, in Angew. Chem., 67, 275 (1955) and Sci. Pharm., 51, 283 (1980) that when thiourea dioxide is reacted with amino group-containing compounds, there usually are produced derivatives of guanidine and of cyanamide through decomposition of thiourea dioxide. In those literatures there is not described at all the preparation of amine substituted products of thiourea dioxide as in the present invention by the said reaction.

SUMMARY OF THE INVENTION

Having made extensive studies about the reaction of thiourea dioxide with primary amines, the present inventors found out a process for effectively preparing amine substituted products of thiourea dioxide of great utility value while preventing the formation of guanidine and cyanamide derivatives. Thus we accomplished the present invention.

More particularly, the present invention resides in a process for preparing an amine-substituted thiourea dioxide by reacting thiourea dioxide and an aliphatic or aromatic primary amine in a neutral or acidic pH range at a temperature sufficient to produce the amine-substituted thiourea dioxide.

DETAILED DESCRIPTION OF THE INVENTION

As the thiourea dioxide used in the present invention, a commercially available reagent or an industrial chemical is employable as it is without the need of purification. Thiourea dioxide is produced in a large amount by the reaction of thiourea and hydrogen peroxide and it is one of great advantages of the present invention that thiourea dioxide is available inexpensively and extremely easily on an industrial scale.

Primary amines employable in the present invention are the compounds of the general formula $RNH_2$ wherein R is not specially limited if only it is an aliphatic or aromatic group, it being usually an alkyl, aralkyl or aryl having not more than 18 carbon atoms. Examples of alkyl are straight or branched chain alkyls represented by $C_nH_{2n+1}$ such as methyl, ethyl, n-propyl, isoproply, butyl, hexyl, octyl and dodecyl. Examples of aralkyl are benzyl and phenylethyl, and examples of aryl are phenyl, methylphenyl and naphthyl. It is to be understood that the primary amines which may be used in the invention are not limited to those just exemplified and that essentially there may be used any primary amines.

The pH range of the reaction system used in the present invention is a neutral or acidic range, more specifically pH 2 to 7, preferably pH 5 to 7. The region lower than 2 in pH should be avoided. The addition of a weakly acidic substance is desirable to adjust the pH of the reaction system to a value in such pH range. Preferred examples of weakly acidic substances are weakly acidic, lower aliphatic, organic acids such as formic acid, acetic acid, propionic acid and butyric acid. But such strongly acidic mineral acids as sulfuric, hydrochloric and phosphoric acids are also employable.

The reaction of thiourea dioxide and a primary amine in the present invention is carried out at a temperature usually in the range of 10° to 80° C., preferably, 25° to 40° C., and atmospheric pressure.

Preferably, the reaction is conducted by dissolving a primary amine in water and/or a water-soluble organic solvent, adjusting pH in the manner described above, adding thiourea dioxide into the resulting solution and making stirring.

Examples of water-soluble organic solvents which may be used in the present invention are those miscible intimately with water and capable of dissolving primary amine salts, such as lower aliphatic alcohols, e.g. methanol, ethanol and 2-propanol; lower aliphatic dihydric alcohol, e.g. ethylene glycol and propylene glycol; as well as acetone and acetonitrile. It is necessary to use these water-soluble organic solvents particularly for salts of aliphatic amines having six or more carbon atoms because these salts are water-insoluble.

It is preferable that the reaction be performed in an atmosphere purged with an inert gas such as nitrogen gas, although it may be carried out in the air.

The reaction in the present invention is chemically formulated as follows:

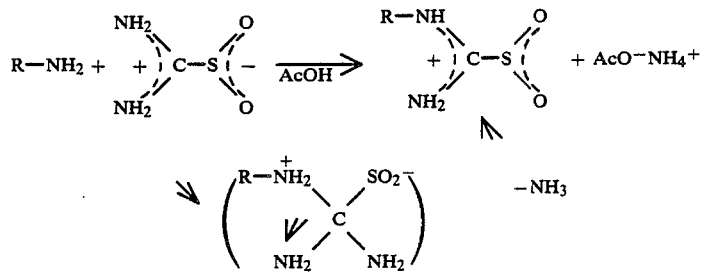

wherein AcOH represents acetic acid as a typical example of acid.

If the amonoamine-substituted thiourea dioxide produced by the above reaction is further reacted with a primary amine, the residual NH₂ in the product will further react to form a diamine-substituted thiourea dioxide.

Therefore, the product of the present invention can be represented by the following general formula:

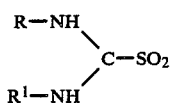

wherein $R^1$ represents R or H.

The thiourea dioxide derivative of the invention thus prepared is inexpensive because the starting materials are easily available, and is soluble in organic solvents, so is effectively applicable to various uses which utilize the characteristics of the thiourea dioxide structure in the field of high polymers and that of organic chemistry.

The present invention will be described below in more detail in terms of working examples thereof, but it is to be understood that the invention is not limited thereto.

EXAMPLE-1

N-methyl thiourea dioxide 9.3 g (0.3 mol) of methylamine and 20 g (0.33 mol) of acetic acid were dissolved in a mixed solvent of 300 ml water and 200 ml methanol in a nitrogen gas atmosphere while the generation of heat was suppressed (pH of the solution: about 6.5). Then, 32.4 g (0.3 mol) of thiourea dioxide was added little by little and stirring was made for 6 hours at room temperature. After the completion of reaction, the solvent was distilled off, leaving a syrupy substance, to which was added 5 ml of ethanol, allowing crystallization to take place, to afford 27.3 g (73.9%) of white crystals of N-methyl thiourea dioxide, m.p. 99°–101° C.

EXAMPLE-2

N-n-butyl-thiourea dioxide 300 ml of water, 43.8 g (0.6 mol) of n-butylamine, 37.8 g (0.63 mol) of acetic acid and 64.9 g (0.6 mol) of thiourea dioxide were stirred at 40° C. for 4 hours in the similar manner as in Example 1 (pH of the solution: about 6.5). Precipitated while crystals were separated by centrifugal separation to afford 42.1 g (85%) of N-n-butyl thiourea dioxide, m.p. 110°–112° C.

EXAMPLE-3

N-n-hexyl thiourea dioxide 300 ml of water, 60.6 g (0.3 mol) of n-hexylamine, 20 g (0.33 mol) of acetic acid and 32.4 g (0.3 mol) of thiourea dioxide were stirred at room temperature for 1.5 hours in the similar manner as in Example 1 (pH of the solution: about 6.0). Precipitated crystals were separated by centrifugal separation to afford 52.1 g (90%) of N-n-hexyl thiourea dioxide, m.p. 93.5°–95.0° C.

EXAMPLE-4

N-n-dodecyl thiourea dioxide

A mixed solvent of 200 ml water and 300 ml ethanol, 92.6 g (0.5 mol) of n-dodecylamine, 31.2 g (0.52 mol) of acetic acid and 54.1 g (0.5 mol) of thiourea dioxide were stirred at room temperature for 1.5 hours in the similar manner as in Example 1 (pH of the solution: about 6.0). Precipitated crystals were separated by centrifugal separation to afford 127.5 g (92%) of N-n-dodecyl thiourea dioxide, m.p. 98.2°–99.0° C.

EXAMPLE-5

N-benzyl thiourea dioxide 200 ml of water, 32.1 g (0.3 mol) of benzylamine, 20 g (0.33 mol) of acetic acid and 32.4 g (0.3 mol) of thiourea dioxide were stirred at room temperature for 1.5 hours in the similar manner as in Example 1 (pH of the solution: about 6.0). Precipitated crystals were separated by centrifugal separation to afford 55.4 g (93%) of N-benzyl thiourea dioxide, m.p. 133°–135° C.

EXAMPLE-6

N-phenyl thiourea dioxide

A mixed solvent of 200 ml water and 200 ml ethanol, 27.9 g (0.3 mol) of aniline, 20 g (0.33 mol) of acetic acid and 32.4 g (0.3 mol) of thiourea dioxide were stirred at 20° C. for 12 hours in the similar manner as in Example 1 (pH of the solution: about 6.0). Precipitated crystals were separated by centrifugal separation to afford 27.8 g (50%) of N-phenyl thiourea dioxide, m.p. 95°–115° C.

EXAMPLE-7

N,N'-dibenzyl thiourea dioxide 32.1 g (0.3 mol) of benzylamine and 20 g (0.33 mol) of acetic acid were dissolved in a mixed solvent of 200 ml water and 200 ml methanol in a nitrogen gas atmosphere while the generation of heat was suppressed (pH of the solution: about 6.0). Then, 59.7 g (0.3 mol) of N-benzyl thiourea dioxide produced in Example-5 was added little by little and stirring was made at room temperature for 1 hour. The reaction solution was rendered strongly acidic with hydrochloric acid and there-after precipitated crystals were separated by centrifugal separation to afford 65.3 g (75%) of N,N'-dibenzyl thiourea dioxide, m.p. 103°–106° C.

EXAMPLE-8

N,N'-diphenyl thiourea dioxide 27.9 g (0.3 mol) of aniline and 20 g (0.33 mol) of acetic acid were dissolved in a mixed solvent of 200 ml water and 200 ml methanol in a nitrogen gas atmosphere while the generation of heat was suppressed (pH of the solution: about 6.0). Then, 55.5 g (0.3 mol) of the N-phenyl thiourea dioxide produced in Example-6 was added little by little and stirring was made at 20° C. for 6 hours. After the completion of the reaction there was obtained 38.5 g (48%) of N,N'-diphenyl thiourea dioxide, m.p. 125°–130° C.

EXAMPLE-9

N-benzyl thiourea dioxide

Reaction was carried out in the same manner as in Example-5 except that 68.6 g (0.35 mol) of 50% sulfuric acid was used as acid (pH of the solution: about 6.0). After the reaction at room temperature for 10 hours there was obtained 41.3 g (69.2%) of N-benzyl thiourea dioxide.

EXAMPLE-10

N,N'-dibenzyl thiourea dioxide 300 ml of ethanol was added to a slurry of the N-benzyl thiourea dioxide obtained in Example-5, allowing the N-benzyl thiourea dioxide to be dissolved therein almost completely (pH of the solution: about 6.0). Further, 32.1 g (0.3 mol) of benzylamine and 20 g (0.33 mol) of acetic acid were added to the resulting solution and stirring was made at room temperature for 1 hour. Precipitated crystals were separated by centrifugal separation to afford 25.4 g (29.2%) of N,N'-dibenzyl thiourea dioxide.

COMPARATIVE EXAMPLE-1

An attempt was made to prepare N-benzyl thiourea dioxide using benzylamine and thiourea dioxide without using acid. The pH of the reaction solution was 9. During reaction at room temperature, thiourea dioxide was decomposed with liberation of sulfur and sulfite ion.

What is claimed is:

1. A process for preparing an amine-substituted thiourea dioxide, comprising reacting thiourea dioxide and an aliphatic or aromatic primary amine in a neutral or acidic pH range.

2. A process as set forth in claim 1, using water and/or a water-soluble organic solvent as a reaction medium.

3. A process as set forth in claim 1 or claim 2, wherein the pH is in the range of 2 to 7.

4. A process as set forth in claim 2 wherein an acid is added to a solution of the aliphatic or aromatic primary amine in water and/or the water soluble organic solvent, in a molar amount equal to or larger than the molar amount of said amine, to adjust the pH, then thiourea dioxide is added to the solution and the reaction is allowed to take place.

5. A process set forth in claim 4 wherein the pH is in the range of 2 to 7.

* * * * *